US011585546B2

(12) United States Patent
Park et al.

(10) Patent No.: US 11,585,546 B2
(45) Date of Patent: Feb. 21, 2023

(54) PHOTOCATALYTIC FILTER AND AIR CONDITIONING DEVICE COMPRISING PHOTOCATALYTIC FILTER

(71) Applicant: Samsung Electronics Co., Ltd., Suwon-si (KR)

(72) Inventors: Hee-jin Park, Seoul (KR); Jee-yeon Kim, Seoul (KR); Yong-won Jeong, Seoul (KR); Sae-mi Kim, Seoul (KR); Jeong-eun Lee, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 159 days.

(21) Appl. No.: 16/767,770

(22) PCT Filed: Aug. 23, 2018

(86) PCT No.: PCT/KR2018/009696
§ 371 (c)(1),
(2) Date: May 28, 2020

(87) PCT Pub. No.: WO2019/164072
PCT Pub. Date: Aug. 29, 2018

(65) Prior Publication Data
US 2020/0363081 A1 Nov. 19, 2020

(30) Foreign Application Priority Data
Feb. 20, 2018 (KR) .......................... 10-2018-0019632

(51) Int. Cl.
*F24F 8/167* (2021.01)
*A61L 9/20* (2006.01)
(Continued)

(52) U.S. Cl.
CPC .............. *F24F 8/167* (2021.01); *A61L 9/205* (2013.01); *B01D 53/007* (2013.01);
(Continued)

(58) Field of Classification Search
None
See application file for complete search history.

(56) References Cited

U.S. PATENT DOCUMENTS 6,063,343 A 5/2000 Say et al.
6,149,717 A 11/2000 Satyapal et al.
(Continued)

FOREIGN PATENT DOCUMENTS

JP 2000-086497 A 3/2000
JP 2000-189835 A 7/2000
(Continued)

OTHER PUBLICATIONS

Merriam-Webster Dictionary. "Plate" Definition and Meaning. https://www.merriam-webster.com/dictionary/plate (Year: 2021).*
(Continued)

*Primary Examiner* — Jelitza M Perez
(74) *Attorney, Agent, or Firm* — Jefferson IP Law, LLP

(57) ABSTRACT

An air conditioning device is disclosed. The present air conditioning device comprises: a photocatalytic filter including a space through which air can pass and having a transition metal oxide formed in a nanotube form on the surface thereof, the transition metal oxide removing gases included in the air and including at least one of $TiO_2$, $ZnO$, $NiO$, and $WO_3$; and a light source for emitting light to the photocatalytic filter.

11 Claims, 12 Drawing Sheets

(51) Int. Cl.
   *B01D 53/00*   (2006.01)
   *B01D 53/86*   (2006.01)
   *B01D 53/88*   (2006.01)
   *B01J 21/06*   (2006.01)
   *B01J 23/06*   (2006.01)
   *B01J 23/30*   (2006.01)
   *B01J 23/755*  (2006.01)
   *B01J 35/00*   (2006.01)
   *F24F 8/10*    (2021.01)
   *F24F 8/22*    (2021.01)
   *F24F 8/30*    (2021.01)

(52) U.S. Cl.
   CPC ..... *B01D 53/8637* (2013.01); *B01D 53/8668* (2013.01); *B01D 53/885* (2013.01); *B01J 21/063* (2013.01); *B01J 23/06* (2013.01); *B01J 23/30* (2013.01); *B01J 23/755* (2013.01); *B01J 35/004* (2013.01); *B01J 35/0013* (2013.01); *F24F 8/10* (2021.01); *F24F 8/22* (2021.01); *F24F 8/30* (2021.01); *A61L 2209/12* (2013.01); *A61L 2209/14* (2013.01); *A61L 2209/16* (2013.01); *B01D 2255/20707* (2013.01); *B01D 2255/20753* (2013.01); *B01D 2255/20776* (2013.01); *B01D 2255/20792* (2013.01); *B01D 2255/802* (2013.01)

(56) References Cited

U.S. PATENT DOCUMENTS

| | | | |
|---|---|---|---|
| 9,365,994 B2 | 6/2016 | Munro | |
| 9,504,958 B2 | 11/2016 | Heidenreich | |
| 2005/0142047 A1 | 6/2005 | Baik et al. | |
| 2010/0239470 A1 | 9/2010 | Pham-Huu et al. | |
| 2011/0194990 A1* | 8/2011 | Hsu | B82Y 30/00 502/182 |
| 2012/0085927 A1 | 4/2012 | Maeng et al. | |
| 2013/0028796 A1* | 1/2013 | Nakatani | B01D 53/8603 422/121 |
| 2015/0320900 A1 | 11/2015 | Goswami et al. | |

FOREIGN PATENT DOCUMENTS

| | | |
|---|---|---|
| JP | 2002-316021 A | 10/2002 |
| JP | 2004-148305 A | 5/2004 |
| JP | 2005-193884 A | 7/2005 |
| JP | 4339661 B2 | 10/2009 |
| KR | 20-0355965 Y1 | 7/2004 |
| KR | 10-0565775 B1 | 3/2006 |
| KR | 10-0826320 B1 | 5/2008 |
| KR | 10-2014-0119334 A | 10/2014 |
| KR | 10-2016-0098631 A | 8/2016 |
| KR | 10-1670006 B1 | 10/2016 |
| KR | 10-2017-0003857 A | 1/2017 |

OTHER PUBLICATIONS

Extended European Search Report dated Nov. 24, 2020, issued in European Application No. 18907358.8.

Korean Office Action with English translation dated Oct. 21, 2022; Korean Appln. No. 10-2018-0019632.

\* cited by examiner

110

PHOTOCATALYTIC FILTER AND AIR CONDITIONING DEVICE COMPRISING PHOTOCATALYTIC FILTER

TECHNICAL FIELD

The disclosure relates to a photocatalytic filter and an air conditioning device comprising the photocatalytic filter, and more particularly, to a photocatalytic filter of which luminescent efficiency is increased using a transition metal oxide having a nanotube structure, and an air conditioning device comprising the photocatalytic filter.

BACKGROUND ART

Recently, in accordance with an increase in a demand for an air purifying device for purifying indoor air due to air pollution, fine dust, yellow dust, or the like, various types of air purifying devices have been produced. For example, there was an air purifying device using a non-woven fabric type filter, an electrical dust collection type electrostatic filter, or the like. However, such a filter may filter dust, but it was difficult for the filter to remove an odor or sterilize bacteria. Therefore, a separate deodorizing filter formed of activated carbon has also been used for the purpose of deodorization. However, the deodorizing filter formed of activated carbon has bad durability, and may not sterilize harmful microorganisms included in the air.

To resolve these problems, a technology of using a photocatalytic material to purify air has been studied, and a typical example of the photocatalytic material may include titanium dioxide ($TiO_2$). Titanium dioxide generates a radical when being applied with an infrared ray, and may sterilize microorganisms and decompose an odor material generating odor with strong oxidizing power of such a radical.

To use the photocatalytic material as described above, separate light sources such as light emitting diodes (LEDs) need to be included in the air purifying device. As the number of light sources is increased, a photocatalytic reaction is accelerated, and thus an air purifying effect may be increased. In this case, however, energy consumption is also increased.

Therefore, there was a demand for an air purifying device to which a photocatalyst that may improve an air purifying effect is applied while reducing energy consumption.

DISCLOSURE

Technical Problem

The disclosure provides a photocatalytic filter of which luminescent efficiency is increased using a transition metal oxide having a nanotube structure, and an air conditioning device comprising the photocatalytic filter.

Technical Solution

According to an embodiment of the disclosure, an air conditioning device includes: a photocatalytic filter including a space through which air may pass and having a surface on which a transition metal oxide is formed in a nanotube form, the transition metal oxide removing gas included in the air and including at least one of $TiO_2$, ZnO, NiO, or $WO_3$; and a light source configured to irradiate the photocatalytic filter with light.

The photocatalytic filter may include a plurality of plates each having a surface on which the transition metal oxide is formed in a nanotube form, and the plurality of plates may be spaced apart from each other to allow the air to pass between the plurality of plates.

The light source may include a plurality of light emitting diodes (LEDs) corresponding to the plurality of plates, respectively.

The air conditioning device may further include: a suction port configured to suck air from the outside; and a discharging port configured to discharge air filtered by the photocatalytic filter to the outside, wherein the air sucked by the suction port moves toward the discharging port, and the plurality of plates are arranged in line at a predetermined angle with respect to a direction in which the air sucked by the suction port moves toward the discharging port.

The predetermined angle and an interval at which the plurality of plates are arranged may be determined based on at least one of a flow rate of the air, a flow velocity of the air, a contact area with the plurality of plates per unit volume of the air, a structure of the air conditioning device, or a layout of the plurality of plates.

Each of the plurality of LEDs may be disposed on a plate that is adjacent to a target plate to be irradiated with light by each of the plurality of LEDs.

The light source may include an LED layer in which a plurality of LEDs that irradiate the plurality of plates with light, respectively, are arranged in line.

A width of each of the plurality of plates may be determined based on a light emission angle of the plurality of LEDs.

The photocatalytic filter may include a first layer in which a plurality of plates are arranged in line at a predetermined interval; and a second layer which is spaced apart from the first layer and in which a plurality of plates are arranged in line at a predetermined interval, and the plurality of plates included in the first layer and the plurality of plates included in the second layer may be arranged to be misaligned with each other.

A plurality of LEDs corresponding to the plurality of plates included in the first layer, respectively, may each be disposed in a space of the second layer corresponding to each of the plurality of plates included in the first layer, and a plurality of LEDs corresponding to the plurality of plates included in the second layer, respectively, may each be disposed in a space of the first layer corresponding to each of the plurality of plates included in the second layer.

The light source may include a third layer including a plurality of LEDs that irradiate the plurality of plates included in the first layer and the plurality of plates included in the second layer with light, respectively.

The photocatalytic filter may include a plate having a plurality of holes through which air may pass.

The light source may include a plurality of LEDs arranged at a predetermined interval based on a light emission angle.

The plurality of holes may each be formed in a region where an intensity of light irradiated on the plate by each of the plurality of LEDs is less than a predetermined value.

According to another embodiment of the disclosure, a photocatalytic filter includes: a transition metal plate including a space through which air may pass; and a transition metal oxide formed in a nanotube form on a surface of the transition metal plate and removing gas included in the air.

The transition metal plate may include a plurality of transition metal plates, and the plurality of transition metal plates may be spaced apart from each other to allow the air to pass between the plurality of transition metal plates.

The plurality of transition metal plates may be arranged in line at a predetermined angle with respect to a direction in which air sucked from the outside moves to be discharged after being filtered.

The predetermined angle and an interval at which the plurality of transition metal plates are arranged may be determined based on at least one of a flow rate of the air, a flow velocity of the air, or a contact area with the plurality of transition metal plates per unit volume of the air.

The photocatalytic filter may include a first layer in which a plurality of transition metal plates are arranged in line at a predetermined interval; and a second layer which is spaced apart from the first layer and in which a plurality of transition metal plates are arranged in line at a predetermined interval, and the plurality of transition metal plates included in the first layer and the plurality of transition metal plates included in the second layer may be arranged to be misaligned with each other.

The transition metal plate may have a plurality of holes through which air may pass.

BEST MODE

Figure 1:
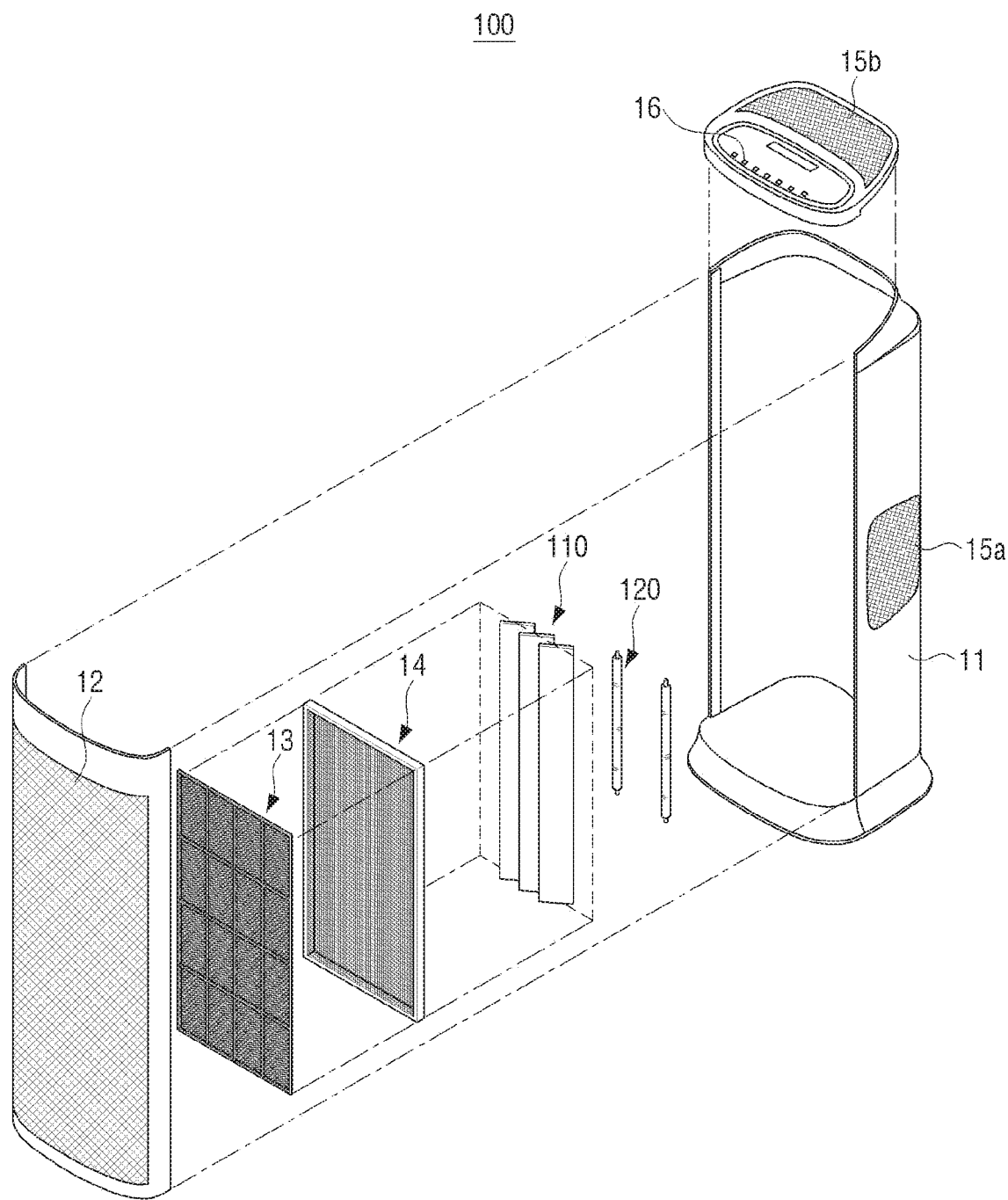
FIG. 1 is an exploded perspective view for describing a configuration of an air conditioning device according to an embodiment of the disclosure in detail.

In describing the disclosure, when it is decided that a detailed description for the known functions or configurations related to the disclosure may unnecessarily obscure the gist of the disclosure, the detailed description therefor will be omitted. In addition, the following terms, terms defined in consideration of functions in the disclosure, may be construed in different ways by the intention of users and operators. Therefore, these terms should be defined on the basis of the contents throughout the specification.

Terms "first", "second", and the like, may be used to describe various components, but the components are not to be construed as being limited by these terms. The terms are used only to distinguish one component from another component.

Terms used in the disclosure are used only to describe specific embodiments rather than limiting the scope of the disclosure. Singular forms used herein are intended to include plural forms unless context explicitly indicates otherwise. It will be further understood that terms "include" or "formed of" used in the specification specify the presence of features, numerals, steps, operations, components, parts, or combinations thereof mentioned in the specification, but do not preclude the presence or addition of one or more other features, numerals, steps, operations, components, parts, or combinations thereof.

In embodiments, a "module" or a "-er/or" may perform at least one function or operation, and be implemented by hardware or software or be implemented by a combination of hardware and software. In addition, a plurality of "modules" or a plurality of "-ers/ors" may be integrated in at least one module and be implemented by at least one processor except for a "module" or a "-er/or" that needs to be implemented by specific hardware.

Hereinafter, embodiments of the disclosure will be described in detail with reference to the accompanying drawings so that those skilled in the art to which the disclosure pertains may easily practice the disclosure. However, the disclosure may be modified in various different forms, and is not limited to embodiments described herein. In addition, in the drawings, portions unrelated to the description will be omitted to obviously describe the disclosure, and similar reference numerals will be used to describe similar portions throughout the specification.

FIG. 1 is an exploded perspective view for describing a configuration of an air conditioning device according to an embodiment of the disclosure in detail.

Referring to FIG. 1, an air conditioning device 100 may include a body 11 forming an appearance, a suction port 12 for sucking air into the air conditioning device 100 from the outside, discharging ports 15a and 15b through which the sucked and filtered air is discharged to the outside, and an inputter 16. Further, a pre-filter 13, a high-efficiency particulate air (HEPA) filter 14, and a photocatalytic filter 110 for purifying air, and a light source 120 may be included in the air conditioning device 100.

Figure 5:
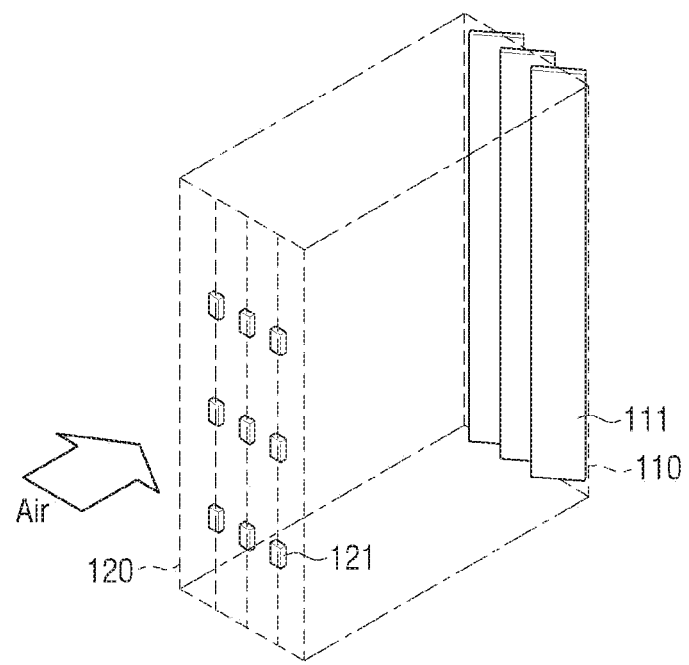
FIG. 5 is a perspective view for describing the air conditioning device of FIG. 4.

The air conditioning device 100 refers to all the devices having a function of purifying air. For example, the air conditioning device 100 may be implemented by an air cleaner, an air conditioner, a humidifier, or the like. The air conditioning device 100 may not only be implemented for the purpose of purifying air in an indoor space, but also be implemented by an air purifying component included in a refrigerator, a drying machine, a clothing management device, or the like that requires a deodorizing function. Alternatively, the air conditioning device 100 may be implemented only by a combination of a photocatalytic filter and a light source as illustrated in FIG. 5.

Relatively large dust particles are primarily filtered out by the pre-filter 13. The HEPA filter 14 is a component for filtering out fine dust or the like that is not filtered out by the pre-filter 13, and may be formed of, for example, a glass fiber.

The photocatalytic filter 110 may perform an antibacterial function, an atmosphere purifying function, a deodorizing function, an antifouling function, and a water purifying function using a photocatalytic material. For example, the photocatalytic filter 110 may sterilize various pathogens and bacteria, remove harmful materials such as a nitrogen oxide (NOx), a sulfur oxide (SOx), and formaldehyde in the air, decompose odor materials such as acetaldehyde, ammonia, and a hydrogen sulfide, decompose organic materials such as cigarette smoke and oil residues, and decompose harmful organic compounds of wastewater.

In FIG. 1, the photocatalytic filter 110 includes a plurality of plates, but the photocatalytic filter 110 may be implemented in various forms such as a single plate form, a mesh form and a honeycomb form.

In addition, although not illustrated, the air conditioning device 100 may further include a deodorizing filter disposed between the pre-filter 13 and the HEPA filter 14 and including activated carbon. The filters may be disposed in a sequence as illustrated in FIG. 1 or be disposed in another sequence.

The light source 120 is a component for irradiating the photocatalytic filter 110 with light. A photocatalytic material of the photocatalytic filter 110 may react to the light irradiated from the light source 120 to remove harmful gases, odor materials, microorganisms, and the like.

The light source 120 may emit light appropriate for causing a photocatalytic reaction in the photocatalytic material included in the photocatalytic filter 110. For example, the light source 120 may be implemented by an elements such as a fluorescent lamp or an incandescent lamp, and a light emitting diode (LED), and may emit light such as white light, red light, green light, blue light, an ultraviolet ray (a wavelength range of 10 to 400 nm), a visible ray (a wavelength range of 400 to 700 nm), an infrared ray (a wavelength range of 700 nm to 1 mm), an NIR (a wavelength range of 0.75 to 1.4 $\mu m$), SWIR (a wavelength range of 1.4 to 3 $\mu m$), MWIR (a wavelength range of 3 to 8 $\mu m$), LWIR (a wavelength range of 8 to 15 $\mu m$), and FIR (a wavelength range of 15 to 1000 $\mu m$).

For example, the light source 120 may include an optical concentrator (for example, a Fresnel lens, a convex lens, or a concave lens), a brightness, an illumination color, a color temperature, light focusing (region), and the like may be controlled by a processor (not illustrated), and the light source 120 may include a color filter.

The light source 120 irradiates the photocatalytic filter 110 with an ultraviolet ray or a visible ray. Although FIG. 1 illustrates the case that the light source 120 is disposed behind the photocatalytic filter 110, the light source 120 is not necessarily limited to being disposed in such a form, but may also be disposed in front of the photocatalytic filter 110 or provided both in front of and behind the photocatalytic filter 110. In addition, the light source 120 is not necessarily disposed to face the photocatalytic filter 110, but may be disposed at any position appropriate for irradiating the photocatalytic filter 110 with light.

Although FIG. 1 illustrates the case that the light source 120 includes two lamps, the light source 120 may include one or three or more lamps. According to another embodiment, the light source 120 may also be implemented by a plurality of LEDs as illustrated in FIG. 5.

Meanwhile, although FIG. 1 illustrates the case that one photocatalytic filter 110 is present in the air conditioning device 100, the air conditioning device 100 may include a plurality of photocatalytic filters.

The inputter 16 may include buttons for inputting various control information related to the air conditioning device 100, such as a power supply button for turning on or off the air conditioning device 100, a timer button for setting a driving time of the air conditioning device 100, and a locking button for restricting manipulation of the inputter to prevent an erroneous manipulation of the inputter 16. Here, each of the input buttons may be a push switch or membrane switch that generates an input signal through pressurization by a user, or a touch switch that generates an input signal through a touch with a part of a user's body.

Meanwhile, the air conditioning device 100 may further include a display for displaying an operation state of the air conditioning device 100. In case that the inputter 16 uses a touch switch manner, the inputter 16 and the display may also be implemented integrally with each other.

Figure 2:
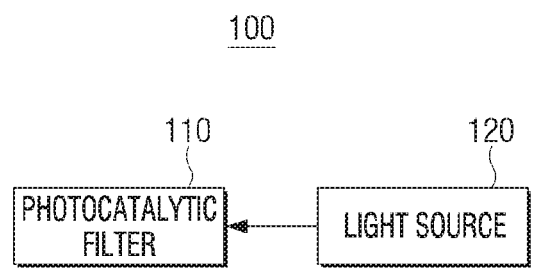
FIG. 2 is a block diagram schematically illustrating a configuration of the air conditioning device according to an embodiment of the disclosure.

FIG. 2 is a block diagram schematically illustrating a configuration of the air conditioning device according to an embodiment of the disclosure.

Referring to FIG. 2, the air conditioning device 100 may include the photocatalytic filter 110 and the light source 120.

Because the photocatalytic filter 110 according to the disclosure may perform the antibacterial function, the atmosphere purifying function, the deodorizing function, the antifouling function, and the water purifying function using the photocatalytic material as described above, the disclosure may be utilized in various fields. For example, the photocatalytic filter 110 may be disposed in a refrigerator, a Kimchi refrigerator, a closet, a shoe rack, a washing machine, a water-purifier tank, a sterilizer, a humidifier, a cleaner, an air conditioner, an air conditioning device, or the like, to perform functions such as a deodorizing function, a water purifying function, a sterilizing function, and an indoor air purifying function. In addition, the photocatalytic filter 110 may also be used in a small product. For example, the photocatalytic filter 100 may be disposed in a smartphone, a tablet personal computer (PC), a smart watch, a patch, or other products (for example, gloves, a band, a necklace, a bracelet, a ring, a headband, an earphone, an earring, and a clothing). In addition, the photocatalytic filter 100 may also be used in a window frame, a wallpaper, a construction, an air conditioning system, a bathroom tile, or the like.

An example in which the photocatalytic filter 100 is installed in the air conditioning device 100 among various application examples described above will hereinafter be described.

The photocatalytic filter 110 may include a photocatalytic material that reacts to the light irradiated from the light source 120 to purify air. Specifically, the photocatalytic filter 110 may include at least one transition metal plate formed of titanium (Ti), zinc (Zn), nickel (Ni), tungsten (W), or the like, and having a surface on which a transition metal oxide is formed in a nanotube form, the transition metal oxide being a photocatalytic material for removing gas included in air. Specifically, the transition metal oxide may include $TiO_2$, $ZnO$, $NiO$, $WO_3$, and the like. Such a transition metal oxide in a nanotube form may be generated by anodizing a surface of the transition metal plate. A structure of the transition metal oxide in a nanotube form will be described later in detail with reference to FIG. 3. Hereinafter, for convenience of explanation, the transition metal will be described as titanium which is a representative example thereof and the transition metal oxide in a nanotube form will be described as a titanium dioxide nanotube (TNT) which is a representative example thereof. Further, hereinafter, a plate having a surface on which a TNT structure as a photocatalytic material is formed will be referred to as a TNT plate. However, in the disclosure, the transition metal is not limited to titanium, and various transition metals in addition to zinc, nickel, and tungsten may be used in the photocatalytic filter.

The photocatalytic filter 110 may include a space through which air may pass. Specifically, the photocatalytic filter 110 may include a single TNT plate or a plurality of TNT plates. In case of including a single TNT plate, the TNT plate may have holes which are formed in partial regions and through which air may pass, and in case of including a plurality of TNT plates, the plurality of TNT plates may be spaced apart from each other to allow air to pass. Here, each of the plurality of TNT plates spaced apart from each other may also have holes.

In case that the photocatalytic filter 110 includes a plurality of TNT plates, the plurality of TNT plates may be arranged in various layouts. For example, the plurality of TNT plates may be arranged at a predetermined angle with respect to an air movement direction in the air conditioning device 100. This is to minimize interruption to a flow of air, and maximize a contact area between air and the TNT plates. Here, the air movement direction refers to a direction of an air movement passage, and may mean a direction in which air sucked by the suction port of the air conditioning device 100 moves to be discharged through the discharging port. For example, in which that the air movement passage between the suction port and the discharging port forms a straight line, a direction from the suction port toward the discharging port may be considered as the air movement direction. Meanwhile, in case that, for example, the suction port is disposed at a side surface of the air conditioning device 100 and the discharging port is disposed at an upper surface of the air conditioning device 100, and thus a direction of the air movement passage changes, the air movement passage is divided into sections based on a point where the direction changes, and a straight-line direction in which the air moves in each section may be regarded as the air movement direction.

Here, an interval at which the plurality of TNT plates are arranged may be determined in consideration of a flow rate of the air, a flow velocity of the air, a contact area with the plurality of TNT plates per unit volume of the air, a structure of the air conditioning device, a layout of the TNT plates, and the like. Specifically, the interval between the plurality of TNT plates may be determined to increase the flow rate of the air, reduce a decrease in flow velocity of the air at the time of passing through the photocatalytic filter 110, or increase the contact area with the plurality of TNT plates per unit volume of the air. The above-described conditions may be considered not only in determining the interval at which the plurality of TNT plates are arranged, but also in determining an angle of the plurality of TNT plates with respect to the air movement direction. Meanwhile, the interval or angle at which the plurality of TNT plates are arranged may also be determined by additionally considering a light emission angle of the light source 120. Here, the light emission angle of the light source 120 refers to a beam divergence angle, and may mean a ratio at which a spot size is increased with respect to a beam movement direction.

Meanwhile, the width of the TNT plate included in the photocatalytic filter 110 may be determined based on the light emission angle of the light source 120. Specifically, the width of the TNT plate may be determined based on the light emission angle of the light source 120 to prevent loss of light emitted from the light source 120 and to prevent any region in the TNT plate from not being irradiated with light. In addition, a distance between the TNT plate and the light source 120 may be additionally considered in determining the width of the TNT plate. Reversely, the distance between the TNT plate and the light source 120 may be determined by using the width of the TNT plate and the light emission angle of the light source 120. As a result, it is possible to minimize energy consumption and maximize luminescent efficiency. An embodiment in which the photocatalytic filter 110 includes a plurality of TNT plates arranged at a predetermined angle while being spaced apart from each other will be described later in detail with reference to FIGS. 4 to 7.

Meanwhile, the plurality of TNT plates included in the photocatalytic filter 110 may be arranged to form a plurality of layers. Specifically, a plurality of layers, each in which the plurality of TNT plates are arranged in line at a predetermined interval, may be included. Here, the plurality of layers may be spaced apart from each other, and the plurality of TNT plates forming the plurality of layers may be arranged to be misaligned with each other. An embodiment of an air conditioning device 100 including such a photocatalytic filter 110 will be described later in detail with reference to FIGS. 8 and 9.

Meanwhile, in case that the photocatalytic filter 110 includes a single TNT plate, the TNT plate may have a plurality of holes for passing air. Here, the hole may be formed in various forms in partial regions of the TNT plate. Specifically, the hole may be formed based on an intensity of light irradiated on the TNT plate. For example, the hole may be formed in a region where the intensity of light irradiated on the TNT plate is less than a predetermine value. By doing so, it is possible to secure a space through which air may flow while maximizing luminescent efficiency.

Meanwhile, although the case that the photocatalytic filter 110 is the TNT plate has been described above, the disclosure is not limited thereto. The photocatalytic filter 110 may also be implemented by a mesh structure or honeycomb structure that has a surface on which a TNT is formed.

The light source 120 is a component for emitting light to the photocatalytic filter 110 for a photocatalytic reaction, and may include a plurality of LEDs. Here, the number of LEDs may be determined based on a quantity of light necessary in the photocatalytic filter 110. Specifically, the plurality of LEDs included in the light source 120 may correspond to the TNT plate, respectively. Here, the correspondence between the plurality of LEDs and the TNT plates may mean that one or more LEDs irradiate only one corresponding TNT plate with light. However, the disclosure is not limited thereto, and one LED may irradiate a plurality of TNT plates with light depending on a layout of the TNT plates.

Here, the plurality of LEDs corresponding to the TNT plates may be arranged at a predetermined interval. Here, the predetermined interval between the plurality of LEDs may be determined based on a light emission angle of the LEDs. Specifically, the interval may be determined based on the light emission angle of the LEDs to prevent regions of the TNT plate that are irradiated with light by each of the plurality of LEDs from overlapping each other and prevent any region from not being irradiated with light. However, the disclosure is not limited thereto. The interval between the LEDs may also be determined to overlap regions where the intensity of light is low so that the regions are irradiated with light having an intensity of a predetermined value or more, because the intensity of light at the center of the region irradiated with light is highest, and the intensity of light becomes low as distance from the center increases.

Meanwhile, the light source 120 may be disposed away from the photocatalytic filter 110 by a predetermined distance. Specifically, the light source 120 may include an LED layer in which a plurality of LEDs that irradiate the plurality of TNT plates with light, respectively, are arranged in line. Here, the TNT plates may be arranged at a predetermined angle with respect to the air movement direction. Such a layout will be described later in detail with reference to FIGS. 4 and 5. Meanwhile, the TNT plates may be arranged in the same direction as the air movement direction. Here, the direction of the TNT plate may mean a direction perpendicular to both arbitrary two straight lines included in a surface of the plate with a starting point where the two straight lines intersect with each other. Such a layout will be described later in detail with reference to FIG. 8.

Meanwhile, the plurality of LEDs included in the light source 120 may each be disposed on a TNT plate that is adjacent to a target TNT plate to be irradiated with light among the plurality of TNT plates. This will be described later in detail with reference to FIG. 6.

Meanwhile, the photocatalytic filter 110 may include a plurality of layers each including the plurality of TNT plates, and in this case, the light source 120 may be disposed between the plurality of TNT plates. Such a layout will be described later with reference to FIG. 9.

As described above, the photocatalytic filter is manufactured by using the TNT plate, and thus it is possible to simplify a manufacturing process and reduce manufacturing costs. Further, various layouts of the TNT plates and the LED may enable minimization of light loss and maximization of photocatalytic reaction efficiency.

Figure 3:
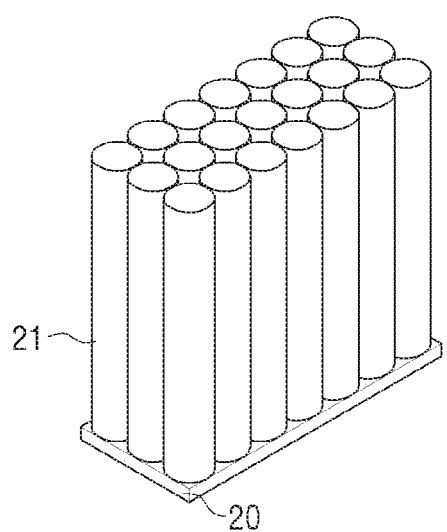
FIG. 3 is a view for describing a structure of a photocatalytic filter according to an embodiment of the disclosure.

FIG. 3 is a view for describing a structure of the photocatalytic filter according to an embodiment of the disclosure.

Referring to FIG. 3, the photocatalytic filter 110 may include a Ti plate 20 and $TiO_2$ nanotubes (TNTs) 21. Specifically, the TNTs are formed on a surface of the Ti plate 20, and may be formed by anodizing a surface of a pure Ti plate.

Once light is irradiated, the TNTs generated as described above generate an electron (e−) having a negative (−) charge and a hole (h+) having a positive (+) charge, the generated electron (e−) reacts to a surface-adsorbed oxygen to generate $O_2$-(superoxide anion), and the hole (h+) reacts to adsorption water to generate a hydroxide (OH radical) which provides strong oxidation. Such an oxidation results in effects such as an antifouling effect, an antibacterial effect, a sterilization effect, a deodorizing effect, a harmful material removing effect, air pollutant reduction effect, and an ultra hydrophilic effect.

FIG. 3 illustrates only a portion of the photocatalytic filter 110, and the TNTs may be formed on all surfaces of the Ti plate 20. As such, $TiO_2$ in a nanotube form has a large surface area, and thus a highly efficient photocatalytic reaction may be expected.

Meanwhile, although the transition metal plate has been described as the Ti plate and the transition metal oxide nanotube has been described as the TNT for convenience of explanation, the disclosure is not limited thereto. In addition to titanium, various transition metals such as zinc, nickel, and tungsten may be used in the photocatalytic filter, and various transition metal oxides formed in a nanotube form on the surface of the transition metal plate may be used in the photocatalytic filter.

Figure 4:
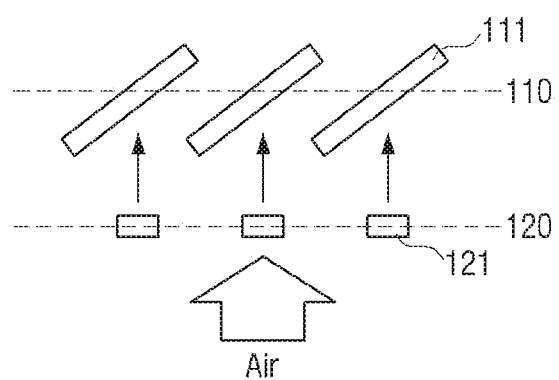
FIGS. 4, 6, 8, and 9 are views for describing various embodiments of an air conditioning device including a photocatalytic filter including a plurality of titanium dioxide nanotube (TNT) plates.

FIG. 4 is a plan view illustrating an embodiment of an air conditioning device including a photocatalytic filter including a plurality of TNT plates when viewed from above.

Referring to FIG. 4, a photocatalytic filter 110 may include a plurality of TNT plates 111. Here, the plurality of TNT plates 111 may be spaced apart from each other at a predetermined interval, and may be arranged in line at a predetermined angle with respect to an air movement direction.

Meanwhile, a light source 120 may include a plurality of LEDs 121 corresponding to the plurality of TNT plates 111, respectively. Specifically, the light source 120 may include an LED layer in which the plurality of LEDs that irradiate the plurality of TNT plates 111 with light, respectively, are arranged in line. Here, the plurality of LEDs 121 may be spaced apart from each other at an interval and to correspond to the plurality of TNT plates 111, respectively.

Meanwhile, although FIG. 4 illustrates the case that the light source 120 is disposed in front of the photocatalytic filter 110, the disclosure is not limited thereto. The light source 120 may be provided behind the photocatalytic filter 110, may be partially disposed in front of the photocatalytic filter 110 and partially disposed behind the photocatalytic filter 110, or may be disposed both in front of and behind the photocatalytic filter 110.

FIG. 5 is a perspective view for describing the air conditioning device of FIG. 4.

Referring to FIG. 5, the photocatalytic filter 110 may include the plurality of TNT plates 111, the plurality of TNT plates 111 may be spaced apart from each other at a predetermined interval, and may be arranged in line at a predetermined angle with respect to the air movement direction.

The plurality of LEDs 121 as the light source 120 may be spaced apart from each other at an interval to correspond to the plurality of TNT plates 111. Here, the plurality of LEDs may be arranged to irradiate one TNT plate with light, and the plurality of LEDs may be arranged at an interval determined based on a light emission angle of the LEDs.

Although FIG. 5 illustrates the case that three LEDs irradiate one TNT plate with light, the disclosure is not limited thereto. The number of LEDs irradiating one TNT plate with light may be two or less or four or more.

Figure 6:
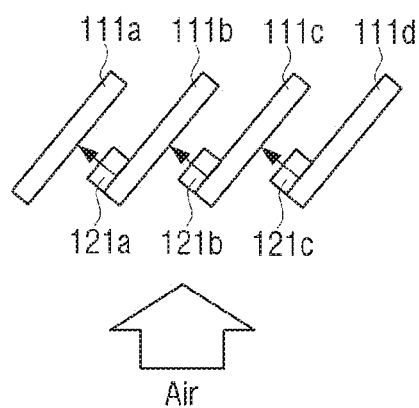

FIG. 6 is a plan view illustrating another embodiment of an air conditioning device including a photocatalytic filter including a plurality of TNT plates when viewed from above.

Referring to FIG. 6, a photocatalytic filter 110 may include a plurality of TNT plates 111a, 111b, 111c, and 111d. Here, the plurality of TNT plates 111a, 111b, 111c, and 111d may be spaced apart from each other at a predetermined interval, and may be arranged in line at a predetermined angle with respect to the air movement direction.

Meanwhile, a light source 120 may include a plurality of LEDs 121a, 121b, and 121c corresponding to the plurality of TNT plates 111a, 111b, 111c, and 111d, respectively. Here, the plurality of LEDs 121a, 121b, and 121c may be spaced apart from each other at an interval to correspond to the plurality of TNT plates 111a, 111b, 111c, and 111d, respectively. In particular, the plurality of LEDs 121a, 121b, and 121c may each be disposed on a TNT plate that is adjacent to a target TNT plate to be irradiated with light by each of the plurality of LEDs.

Specifically, a first LED 121a irradiating a first TNT plate 111a with light may be disposed on a second TNT plate 111b that is adjacent to the first TNT plate 111a. Further, although not illustrated, a fourth LED (not illustrated) irradiating a fourth TNT plate 111d with light may be disposed on a fifth TNT plate (not illustrated) that is adjacent to the fourth TNT plate 111d.

Meanwhile, although FIG. 6 illustrates the case that the LEDs are each disposed on a back surface of the TNT plate based on the air movement direction, the disclosure is not limited thereto. In actual implementation, the LEDs may each be disposed on a front surface of the TNT plate, or the LEDs may be disposed on both the front surface and the back surface of the TNT plate.

Although FIG. 6 illustrates the case that the LED is disposed at one end of the TNT plate, the disclosure is not limited thereto. The LED may be disposed at any position based on the angle of or the interval between the TNT plates, as long as the position is a position where luminescent efficiency is most excellent in the surface of the TNT plate.

Figure 7:
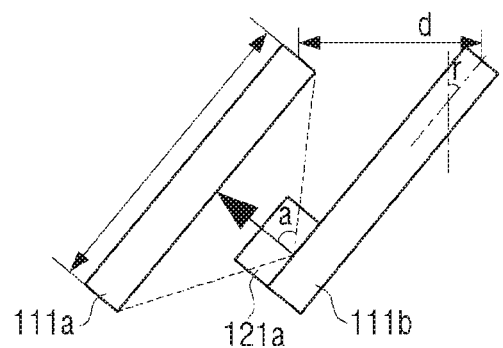
FIG. 7 is a diagram for describing various disposition conditions of a plurality of TNT plates included in a photocatalytic filter according to an embodiment of the disclosure.

FIG. 7 is a diagram for describing various disposition conditions of the plurality of TNT plates included in the photocatalytic filter according to an embodiment of the disclosure.

Referring to FIG. 7, the first TNT plate 111a and the second TNT plate 111b may be arranged at an interval of d. Further, the first TNT plate 111a and the second TNT plate 111b may be arranged at an angle of r with respect to the air movement direction.

Here, the interval d or the angle r at which the first TNT plate 111a and the second TNT plate 111b are arranged may be determined in consideration of a flow rate, a flow velocity and a contact area with the TNT plate per unit volume of air passing through the photocatalytic filter, a structure of the air conditioning device, a layout of the TNT plates, and the like. In addition, the interval d or the angle r at which the first TNT plate 111a and the second TNT plate 111b are arranged may be determined by additionally considering a light emission angle a of the LED 121a and a distance between the LED 121a and the first TNT plate 111a irradiated with light by the LED 121a.

Meanwhile, the first TNT plate 111a may have a width of l. Here, the width l of the first TNT plate 111a may be determined by considering the light emission angle a of the LED 121 and the distance between the LED 121 and the first TNT plate 111a irradiated with light by the LED 121. Specifically, the width l of the first TNT plate 111a may be determined to minimize loss of light emitted from the LED 121 and to prevent any region from not being irradiated with light. Meanwhile, the second TNT plate 111b may have the same width as the first TNT plate 111a, or may have a width different from that of the first TNT plate 111a.

Figure 8:
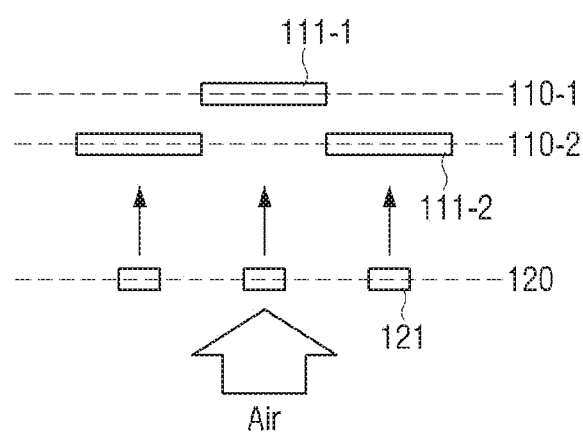

FIG. 8 is a plan view illustrating a still another embodiment of an air conditioning device including a photocatalytic filter including a plurality of TNT plates when viewed from above.

Referring to FIG. 8, a photocatalytic filter 110 may include a first layer 110-1 in which a plurality of TNT plates 111-1 are arranged in line at a predetermined interval, and a second layer 110-2 in which a plurality of TNT plates 111-2 are arranged in line at a predetermined interval. Here, the first layer 110-1 and the second layer 110-2 may be spaced apart from each other. Further, the plurality of TNT plates 111-1 included in the first layer 110-1 and the plurality of TNT plates 111-2 included in the second layer 110-2 may be arranged to be misaligned with each other. Here, the misalignment of the plurality of TNT plates 111-1 and the plurality of TNT plates 111-2 means that the TNT plates 111-1 included in the first layer 110-1 and the TNT plates 111-2 included in the second layer 110-2 do not completely overlap each other, but the TNT plates 111-1 included in the first layer 110-1 and the TNT plates 111-2 included in the second layer 110-2 may partially overlap each other.

Further, a light source 120 may include a third layer including a plurality of LEDs irradiating each of the plurality of TNT plates 111-1 included in the first layer 110-1 and the plurality of TNT plates 111-2 included in the second layer 110-2 with light.

Figure 9:
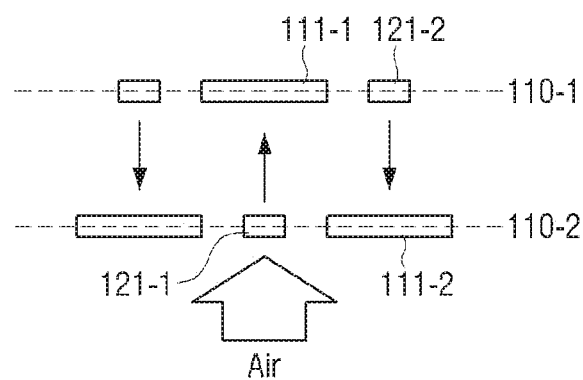

FIG. 9 is a plan view illustrating a further still another embodiment of an air conditioning device including a photocatalytic filter including a plurality of TNT plates when viewed from above.

Referring to FIG. 9, a photocatalytic filter 110 may include a first layer 110-1 in which a plurality of TNT plates 111-1 are arranged in line at a predetermined interval, and a second layer 110-2 in which a plurality of TNT plates 111-2 are arranged in line at a predetermined interval. Here, the first layer 110-1 and the second layer 110-2 may be spaced apart from each other. Further, the plurality of TNT plates 111-1 included in the first layer 110-1 and the plurality of TNT plates 111-2 included in the second layer 110-2 may be arranged to be misaligned with each other.

Further, a plurality of LEDs 121-1 corresponding to the plurality of TNT plates 111-1 included in the first layer 110-1 may be disposed in a space of the second layer 110-2 corresponding to the plurality of TNT plates 111-1. Specifically, the plurality of TNT plates 111-1 included in the first layer 110-1 and the plurality of TNT plates 111-2 included in the second layer 110-2 are arranged to be misaligned with each other. Therefore, in the second layer 110-2, a region corresponding to the TNT plate 111-1 included in the first layer 110-1 is a spacing between the plurality of TNT plates 111-2 included in the second layer 110-2, and the plurality of LEDs 121-1 corresponding to the TNT plates 111-1 included in the first layer 110-1 may be disposed in the spacing between the plurality of TNT plates 111-2 included in the second layer 110-2. Similarly, a plurality of LEDs 121-2 corresponding to the plurality of TNT plates 111-2 included in the second layer 110-2 may be disposed in a space of the first layer 110-1 corresponding to the plurality of TNT plates 111-2. As the plurality of LEDs 121-1 are disposed between the plurality of TNT plates 111-2, and the plurality of LEDs 121-2 are disposed between the plurality of TNT plates 111-1, the photocatalytic filter 110 having the same surface area with only two layers and without a separate LED layer may be manufactured, and thus it is possible to achieve size reduction of the air conditioning device.

Figure 10:
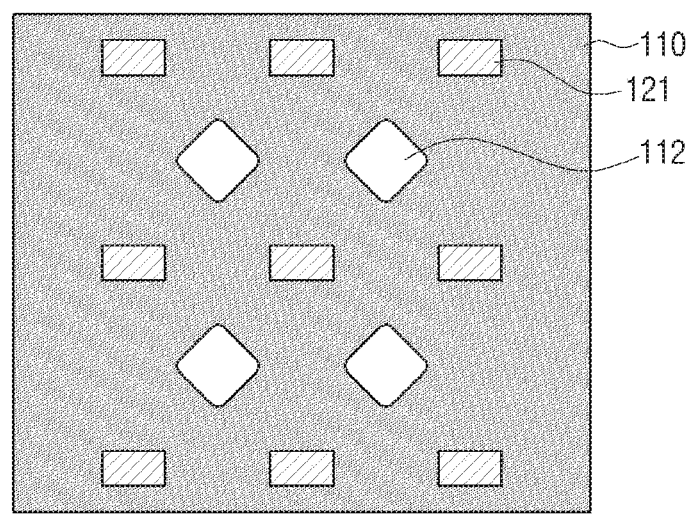
FIGS. 10 and 12 are views for describing various embodiments of a photocatalytic filter including a TNT plate having holes.

FIG. 10 is a view for describing an embodiment of a photocatalytic filter including a TNT plate having holes. Specifically, FIG. 10 is a front view of the photocatalytic filter when viewed in an air movement direction.

Referring to FIG. 10, a photocatalytic filter 110 may include a single TNT plate having holes 112 for passing air. Here, the position and the size of the hole may be determined in consideration of a region where the intensity of light irradiated on a TNT plate by each of a plurality of LEDs 121 is less than a predetermined value, as illustrated in FIG. 11.

Figure 11:
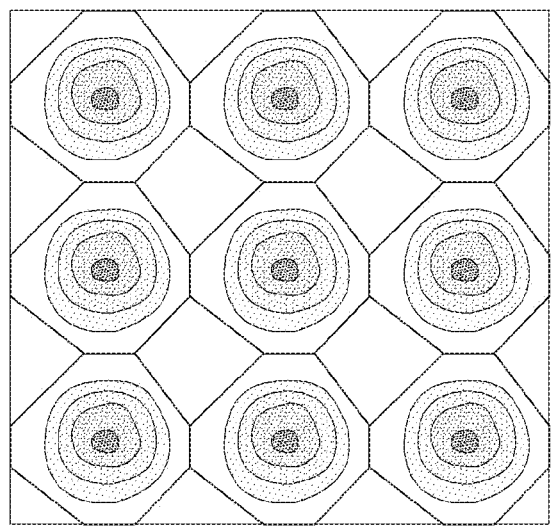
FIG. 11 is a view for describing an embodiment of a condition for determining a region in which the hole is to be formed in the TNT plate of FIG. 10.

In FIG. 11, the darkness of a region is in proportion to the intensity of light. A darker region is a region where the intensity of light is high, and a paler region is a region where the intensity of light is low. Referring to FIG. 11, it may be seen that the intensity of light is highest in a region where the LED is positioned, and the intensity of light decreases as distance from the region where the LED is positioned increases. Referring to this, the hole may be formed in the region where the intensity of light irradiated on the TNT plate is less than the predetermine value.

Meanwhile, FIG. 10 illustrates the case that the hole 112 has a diamond shape for convenience of explanation. However, in actual implementation, the shape of the hole 112 is not particularly limited and may be a circular shape, a polygonal shape, or the like.

Meanwhile, the position and the shape of the hole 112 formed in the photocatalytic filter 110 are not limited to those illustrated in FIG. 10. According to another embodiment, the hole 112 may be formed as illustrated in FIG. 12.

Figure 12:
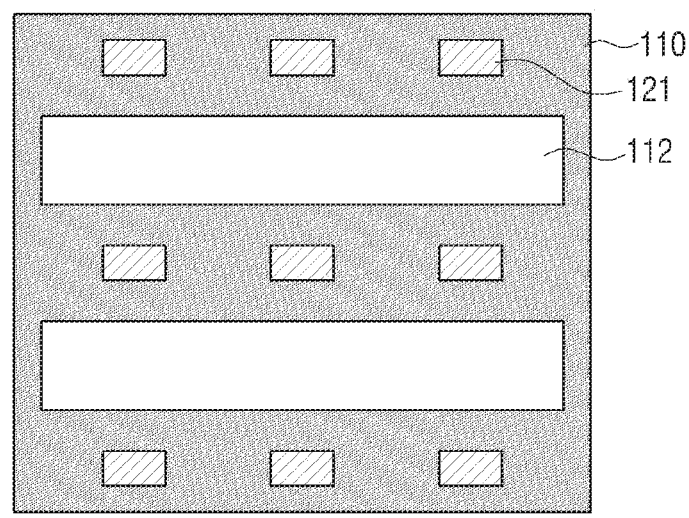

Referring to FIG. 12, a hole 112 formed in a photocatalytic filter 110 may have a size larger than that of the hole illustrated in FIG. 10. The hole 112 of FIG. 12 is also formed based on the intensity of light irradiated from the LED 121.

However, the hole 112 as illustrated in FIG. 12 may also be formed by additionally considering a flow rate of air or a flow velocity of air.

Meanwhile, although the transition metal plate has been described as the Ti plate and the transition metal oxide nanotube has been described as the TNT in FIGS. 4 to 12 for convenience of explanation, the disclosure is not limited thereto. In addition to titanium, various transition metals such as zinc, nickel, and tungsten, and various transition metal oxides formed in a nanotube form may be used in the photocatalytic filter.

As described above, according to various embodiments of the disclosure, it is possible to manufacture a photocatalytic filter of which luminescent efficiency is increased, while minimizing manufacturing costs.

Although embodiments of the disclosure have been illustrated and described hereinabove, the disclosure is not limited to the abovementioned specific embodiments, but may be variously modified by those skilled in the art to which the disclosure pertains without departing from the gist of the disclosure as disclosed in the accompanying claims. These modifications should also be understood to fall within the scope and spirit of the disclosure.

The invention claimed is:

1. An air conditioning device comprising:
   a photocatalytic filter including a plurality of transition metal plates having a surface on which a transition metal oxide is formed as a plurality of nanotubes thereon, wherein the plurality of transition metal plates are spaced apart from each other to allow air to pass between the plurality of transition metal plates, and wherein the transition metal oxide removes gas included in the air and includes at least one of $TiO_2$, ZnO, NiO, or $WO_3$; and
   a light source configured to irradiate the photocatalytic filter with light, the light source including a plurality of light emitting diodes (LEDs) corresponding to the plurality of transition metal plates, respectively, wherein the plurality of LEDs is disposed on a transition metal plate that is adjacent to a target transition metal plate to be irradiated with light by each of the plurality of LEDs,
   wherein a width of a first transition metal plate among the plurality of transition metal plates is determined based on a light emission angle of a first LED corresponding to the first transition metal plate and a distance between the first transition metal plate and the first LED.

2. The air conditioning device as claimed in claim 1, further comprising:
   a suction port configured to suck air from outside; and
   a discharging port configured to discharge air filtered by the photocatalytic filter to the outside,
   wherein the air sucked by the suction port moves toward the discharging port, and
   the plurality of transition metal plates are arranged in line at a predetermined angle with respect to a direction in which the air sucked by the suction port moves toward the discharging port.

3. The air conditioning device as claimed in claim 2, wherein the predetermined angle and an interval at which the plurality of transition metal plates are arranged are determined based on at least one of a flow rate of the air, a flow velocity of the air, a contact area with the plurality of transition metal plates per unit volume of the air, a structure of the air conditioning device, or a layout of the plurality of transition metal plates.

4. The air conditioning device as claimed in claim 2, wherein the light source includes an LED layer in which a plurality of LEDs that irradiate the plurality of transition metal plates with light, respectively, are arranged in line.

5. The air conditioning device as claimed in claim 1, wherein a width of each of the plurality of transition metal plates is determined based on a light emission angle of the plurality of LEDs.

6. The air conditioning device as claimed in claim 1, wherein the photocatalytic filter includes:
   a first layer in which a plurality of transition metal plates are arranged in line at a predetermined interval; and
   a second layer which is spaced apart from the first layer and in which a plurality of transition metal plates are arranged in line at a predetermined interval, and
   the plurality of transition metal plates included in the first layer and the plurality of transition metal plates included in the second layer are arranged to be misaligned with each other.

7. The air conditioning device as claimed in claim 6, wherein a plurality of LEDs corresponding to the plurality of transition metal plates included in the first layer, respectively, are each disposed in a space of the second layer corresponding to each of the plurality of transition metal plates included in the first layer, and
   a plurality of LEDs corresponding to the plurality of transition metal plates included in the second layer, respectively, are each disposed in a space of the first layer corresponding to each of the plurality of transition metal plates included in the second layer.

8. The air conditioning device as claimed in claim 6, wherein the light source includes a third layer including a plurality of LEDs that irradiate the plurality of transition metal plates included in the first layer and the plurality of transition metal plates included in the second layer with light, respectively.

9. The air conditioning device as claimed in claim 1, wherein at least one transition metal plate of the plurality of transition metal plates has a plurality of holes through which air passes.

10. The air conditioning device as claimed in claim 9, wherein the light source includes a plurality of LEDs arranged at a predetermined interval based on a light emission angle.

11. The air conditioning device as claimed in claim 10, wherein the plurality of holes are each formed in a region where an intensity of light irradiated on at least one transition metal plate of the plurality of transition metal plates by each of the plurality of LEDs is less than a predetermined value.

* * * * *